(12) United States Patent
Schütz et al.

(10) Patent No.: US 7,858,299 B2
(45) Date of Patent: *Dec. 28, 2010

(54) METHOD FOR DETECTING AND FOR REMOVING ENDOTOXIN

(75) Inventors: Michael Schütz, Regensburg (DE); Roman Meyer, Schmidmühlen (DE); Holger Grallert, Pentling (DE); Stefan Miller, Regensburg (DE)

(73) Assignee: Hyglos Invest GmbH, Bernried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/510,540

(22) Filed: Jul. 28, 2009

(65) Prior Publication Data
US 2010/0028857 A1     Feb. 4, 2010

Related U.S. Application Data

(63) Continuation of application No. 10/519,259, filed as application No. PCT/DE03/02096 on Jun. 24, 2003, now Pat. No. 7,585,620.

(30) Foreign Application Priority Data

Jun. 24, 2002   (DE) ................. 102 28 133
Feb. 24, 2003   (DE) ................. 103 07 793

(51) Int. Cl.
*C12Q 1/70* (2006.01)
*C12Q 1/00* (2006.01)
*G01N 33/53* (2006.01)

(52) U.S. Cl. ................... 435/5; 435/4; 435/7.1
(58) Field of Classification Search ........................ None
See application file for complete search history.

(56) References Cited

U.S. PATENT DOCUMENTS 5,990,301 A    11/1999    Colpan et al. ............... 536/25.4
7,087,376 B2    8/2006    Miller ............................. 435/5

FOREIGN PATENT DOCUMENTS

| GB | 2192633 | 6/1986 |
|---|---|---|
| WO | WO 9414837 | 7/1994 |
| WO | WO 9915676 | 1/1999 |
| WO | WO 0008463 | 2/2000 |
| WO | WO 0127289 | 4/2001 |
| WO | WO 0166718 | 9/2001 |

OTHER PUBLICATIONS

Baxa et al., "Interactions of phage P22 tails with their cellular receptor, *Salmonella* O-antigen polysaccharides," *Biophysical J.*, 71: 2040-2048, 1996.
Cliff et al., "A comparative study of the accurate measurement of endotoxin in liposome encapsulated hemoglobin," *Artif. Cells Blood Substit. Immobil. Biotechnol.*, 23(3):331-336, 1995.
Giannella, "Salmonella," *MedMicro*, Chapter 21, 1-10, Webdate: Aug. 25, 2008.
Nesper et al., "Characterization of *Vibrio cholerae* O1 antigen as the bacteriophage K139 receptor and identification of IS*1004* insertions aborting O1 antigen biosynthesis," *J. Bacterio.*, 182(18):5097-5104, 2000.
Office Action, issued in U.S. Appl. No. 10/519,259, mailed Feb. 2, 2007.
Office Action, issued in U.S. Appl. No. 10/519,259, mailed May 2, 2007.
Office Action, issued in U.S. Appl. No. 10/519,259, mailed Oct. 29, 2007.
Office Action, issued in U.S. Appl. No. 10/519,259, mailed Feb. 20, 2008.
Office Action, issued in U.S. Appl. No. 10/519,259, mailed May 1, 2008.
Office Action, issued in U.S. Appl. No. 10/519,259, mailed Aug. 29, 2008.
Office Action, issued in U.S. Appl. No. 10/519,259, mailed Mar. 31, 2009.
Petsch et al. "Endotoxin removal from protein solutions," *J. Biotechnol.*, 76:97-119, 2000.
Sun et al., "Use of bioluminescent *salmonella* for assessing the efficiency of constructed phage-based biosorbent," *J. Indust. Microbiol. Biotech.*, 25:273-275, 2000.
Suzuki et al., "Specific interaction of fused H protein of bacteriophage φX174 with receptor lipopolysaccharides," *Virus Research*, 60: 95-99, 1999.
Goldbaum et al., "Removal of LPS from a *Brucella* cytoplasmic fraction by affinity chromatography with an anti-LPS monoclonal antibody as immunosorbent," *J. Med. Microbiol.*, 40:174-178, 1994.
Office Communication, issued in Japanese Patent Application No. 10-2004-70210018, dated Jul. 20, 2010. (English translation).

*Primary Examiner*—Maryam Monshipouri
*Assistant Examiner*—Marsha M Tsay
(74) *Attorney, Agent, or Firm*—Fulbright & Jaworski

(57) ABSTRACT

The invention relates to a method for identifying endotoxins for eliminating said endotoxins from a sample, with the aid of bacteriophage tail proteins.

17 Claims, 9 Drawing Sheets

FIG. 7

Figure 1:
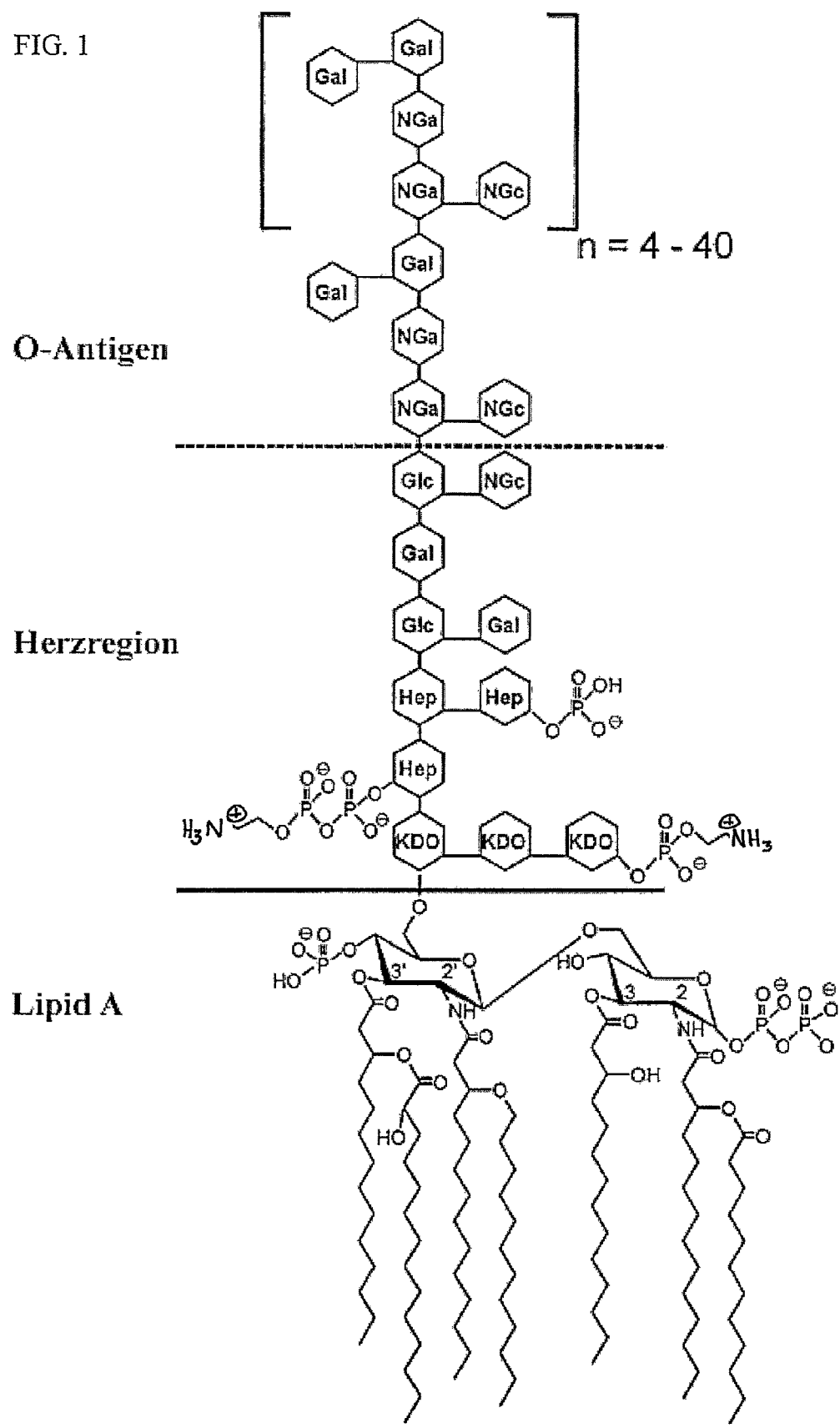

| Endotoxin-Struktur | E. coli Stamm | p12-Bindung |
|---|---|---|
| KDO-LipidA<br>\|<br>KDO<br>\|<br>KDO | D21f2 | - |
| Hep-Hep-KDO-LipidA<br>\|      \|<br>Hep   KDO<br>         \|<br>        KDO | D21f1 | + |
| Glc-Hep-Hep-KDO-LipidA<br>      \|      \|<br>    Hep   KDO<br>           \|<br>           KDO | D21e8 | + |
| Glc-Hep-Hep-KDO-LipidA<br>\|   \|    \|<br>Gal Hep  KDO<br>          \|<br>         KDO | D21e7 | + |
| GlcN-Glc-Glc-Glc-Glc-Hep-Hep-KDO-LipidA<br>                      \|    \|<br>            Gal Hep  KDO<br>                       \|<br>                     KDO | D21 | + |

| pH | $K_d$ |
|---|---|
| 6,0 | 3,09 E-07 |
| 7,5 | 6,85 E-08 |
| 8,0 | 5,86 E-08 |
| 8,5 | 7,86 E-08 |
| 9,0 | 3,29 E-08 |
| 10,0 | 1,55 E-07 |

SEQUENCE LISTING

<160> NUMBER OF SEQ ID NOS: 8

<210> SEQ ID NO 1
<211> LENGTH: 78
<212> TYPE: DNA
<213> ORGANISM: artificial sequence
<220> FEATURE:
<223> OTHER INFORMATION: Primer

<400> SEQUENCE: 1
gaaggaacta gtcatatggc tagctggagc cacccgcagt tcgaaaaagg cgccagtaat      60
aatacatatc aacacgtt      78

<210> SEQ ID NO 2
<211> LENGTH: 54
<212> TYPE: DNA
<213> ORGANISM: artificial sequence
<220> FEATURE:
<223> OTHER INFORMATION: Primer

<400> SEQUENCE: 2
acgcgcaaag cttgtcgacg gatcctatca ttcttttacc ttaattatgt agtt    54

<210> SEQ ID NO 3
<211> LENGTH: 78
<212> TYPE: DNA
<213> ORGANISM: artificial sequence
<220> FEATURE:
<223> OTHER INFORMATION: Primer

<400> SEQUENCE: 3
gaaggaacta gtcatatggc ttgttggagc cacccgcagt tcgaaaaagg cgccagtaat    60
aatacatatc aacacgtt    78

<210> SEQ ID NO 4
<211> LENGTH: 78
<212> TYPE: DNA
<213> ORGANISM: artificial sequence
<220> FEATURE:
<223> OTHER INFORMATION: Primer

<400> SEQUENCE: 4
gaaggaacta gtcatatggc tagctggagc cacccgcagt tcgaaaaagg cgcctgtaat    60
aatacatatc aacacgtt    78

<210> SEQ ID NO 5
<211> LENGTH: 19
<212> TYPE: PRT
<213> ORGANISM: artificial sequence
<220> FEATURE:
<223> OTHER INFORMATION: Tag for targeted Biotinylation

<400> SEQUENCE: 5

Met Ala Ser Trp Ser His Pro Gln Phe Glu Lys Gly Ala Ser Asn Asn
1               5                   10                  15

Thr Tyr Gln

<210> SEQ ID NO 6
<211> LENGTH: 19
<212> TYPE: PRT
<213> ORGANISM: artificial sequence
<220> FEATURE:
<223> OTHER INFORMATION: Tag for targeted Biotinylation

<400> SEQUENCE: 6

Met Ala Cys Trp Ser His Pro Gln Phe Glu Lys Gly Ala Ser Asn Asn
1               5                   10                  15

Thr Tyr Gln

<210> SEQ ID NO 7
<211> LENGTH: 19
<212> TYPE: PRT
<213> ORGANISM: artificial sequence
<220> FEATURE:
<223> OTHER INFORMATION: Tag for targeted Biotinylation

<400> SEQUENCE: 7

Met Ala Ser Trp Ser His Pro Gln Phe Glu Lys Gly Ala Cys Asn Asn
1               5                   10                  15

Thr Tyr Gln

<210> SEQ ID NO 8
<211> LENGTH: 539
<212> TYPE: PRT
<213> ORGANISM: artificial sequence
<220> FEATURE:
<223> OTHER INFORMATION: P12 with a tag for targeted Biotinylation

<400> SEQUENCE: 8

Met Ala Ser Trp Ser His Pro Gln Phe Glu Lys Gly Ala Ser Asn Asn
1               5                   10                  15

Thr Tyr Gln His Val Ser Asn Glu Ser Arg Tyr Val Lys Phe Asp Pro
                20                  25                  30

Thr Asp Thr Asn Phe Pro Pro Glu Ile Thr Asp Val Gln Ala Ala Ile
            35                  40                  45

Ala Ala Ile Ser Pro Ala Gly Val Asn Gly Val Pro Asp Ala Ser Ser
        50                  55                  60

Thr Thr Lys Gly Ile Leu Phe Leu Ala Thr Glu Gln Glu Val Ile Asp
65                  70                  75                  80

Gly Thr Asn Asn Thr Lys Ala Val Thr Pro Ala Thr Leu Ala Thr Arg
                85                  90                  95

Leu Ser Tyr Pro Asn Ala Thr Glu Ala Val Tyr Gly Leu Thr Arg Tyr
            100                 105                 110

Ser Thr Asp Asp Glu Ala Ile Ala Gly Val Asn Asn Glu Ser Ser Ile
        115                 120                 125

Thr Pro Ala Lys Phe Thr Val Ala Leu Asn Asn Val Phe Glu Thr Arg
130                 135                 140

Val Ser Thr Glu Ser Ser Asn Gly Val Ile Lys Ile Ser Ser Leu Pro
145                 150                 155                 160

Gln Ala Leu Ala Gly Ala Asp Asp Thr Thr Ala Met Thr Pro Leu Lys
                165                 170                 175

Thr Gln Gln Leu Ala Val Lys Leu Ile Ala Gln Ile Ala Pro Ser Lys
            180                 185                 190

Asn Ala Ala Thr Glu Ser Glu Gln Gly Val Ile Gln Leu Ala Thr Val
        195                 200                 205

Ala Gln Ala Arg Gln Gly Thr Leu Arg Glu Gly Tyr Ala Ile Ser Pro
210                 215                 220

Tyr Thr Phe Met Asn Ser Thr Ala Thr Glu Glu Tyr Lys Gly Val Ile
225                 230                 235                 240

Lys Leu Gly Thr Gln Ser Glu Val Asn Ser Asn Ala Ser Val Ala
                245                 250                 255

Val Thr Gly Ala Thr Leu Asn Gly Arg Gly Ser Thr Ser Met Arg
            260                 265                 270

Gly Val Val Lys Leu Thr Thr Thr Ala Gly Ser Gln Ser Gly Gly Asp
        275                 280                 285

Ala Ser Ser Ala Leu Ala Trp Asn Ala Asp Val Ile His Gln Arg Gly
290                 295                 300

Gly Gln Thr Ile Asn Gly Thr Leu Arg Ile Asn Asn Thr Leu Thr Ile
305                 310                 315                 320

Ala Ser Gly Gly Ala Asn Ile Thr Gly Thr Val Asn Met Thr Gly Gly
                325                 330                 335

-continued

```
Tyr Ile Gln Gly Lys Arg Val Val Thr Gln Asn Glu Ile Asp Arg Thr
            340                 345                 350
Ile Pro Val Gly Ala Ile Met Met Trp Ala Ala Asp Ser Leu Pro Ser
        355                 360                 365
Asp Ala Trp Arg Phe Cys His Gly Gly Thr Val Ser Ala Ser Asp Cys
        370                 375                 380
Pro Leu Tyr Ala Ser Arg Ile Gly Thr Arg Tyr Gly Gly Ser Ser Ser
385                 390                 395                 400
Asn Pro Gly Leu Pro Asp Met Arg Gly Leu Phe Val Arg Gly Ser Gly
                405                 410                 415
Arg Gly Ser His Leu Thr Asn Pro Asn Val Asn Gly Asn Asp Gln Phe
                420                 425                 430
Gly Lys Pro Arg Leu Gly Val Gly Cys Thr Gly Gly Tyr Val Gly Glu
            435                 440                 445
Val Gln Lys Gln Gln Met Ser Tyr His Lys His Ala Gly Gly Phe Gly
        450                 455                 460
Glu Tyr Asp Asp Ser Gly Ala Phe Gly Asn Thr Arg Arg Ser Asn Phe
465                 470                 475                 480
Val Gly Thr Arg Lys Gly Leu Asp Trp Asp Asn Arg Ser Tyr Phe Thr
                485                 490                 495
Asn Asp Gly Tyr Glu Ile Asp Pro Ala Ser Gln Arg Asn Ser Arg Tyr
                500                 505                 510
Thr Leu Asn Arg Pro Glu Leu Ile Gly Asn Glu Thr Arg Pro Trp Asn
            515                 520                 525
Ile Ser Leu Asn Tyr Ile Ile Lys Val Lys Glu
        530                 535
```

METHOD FOR DETECTING AND FOR REMOVING ENDOTOXIN

This application is a continuation of application Ser. No. 10/519,259, filed Dec. 21, 2004, which application claims priority to PCT/DE 2003/002096, filed on Jun. 24, 2003, the entire contents of both of which are hereby incorporated by reference.

The present invention relates to a method for detecting and for depleting endotoxins from a sample.

Endotoxin (ET) describes a family of lipopolysaccharides which together with proteins and phospholipids form the outer cell wall of Gram-negative bacteria. Endotoxins occur exclusively in this bacterial group and play an important role in the organisation, stability and barrier function of the outer membrane. Numerous bacteriophages use endotoxin or general lipopolysaccharide for specific detection of their host bacteria.

All endotoxin variants comprise a heteropolysaccharide which is bonded covalently to lipid A (Holst, O., 1999, Chemical structure of the core region of lipopolysaccharides. In: Endotoxin in health and disease (Brade, H., Morrison, D. C., Opal, S., Vogel, S. eds.), Marcel Dekker Inc. New York). Lipid A anchors endotoxin in the outer bacterial membrane. The heteropolysaccharide, which comprises a core oligosaccharide and the O antigen, appears in the surrounding solution and determines the serological identity of the bacterium. The O antigen comprises repetitive oligosaccharide units, the composition of which is strain-specific (see in this context Holst et al., above). Characteristic building blocks of the core oligosaccharide are 2-keto-3-deoxyoctonate (KDO) and L-glycero-D-mannoheptose (Hep).

The most conservative part of endotoxin of different types is the lipid A. The inner core region is preserved similarly to lipid A, the outer core region already has a higher variation. The inner core region, KDO and lipid A itself carry a plurality of phosphate groups as substituents and are therefore responsible for the negative charge of endotoxin. Furthermore, the phosphate groups on the lipid A and on the core region can be substituted variably with arabinose, ethanolamine and phosphate. Individual saccharide building blocks of the O antigen are acetylated, sialated or glycosylated. The O antigen varies in addition with respect to the number of repetitive units, for which reason the endotoxin population of each bacterium has a certain heterogeneity (Palva E. T., Makela P. H., Lipopolysaccharide heterogeneity in *Salmonella typhimurium* analysed by sodium dodecyl sulfate polyacrylamide gel electrophoresis. Eur J Biochem. 1980;107(1):137-43; Goldman R. C., Leive L., Heterogeneity of antigenic-side-chain length in lipopolysaccharide from *Escherichia coli* O111 and *Salmonella typhimurium* LT2, Eur J Biochem. 1980;107(1): 145-53).

Endotoxins are biomolecules which can be found in practically all aqueous solutions without corresponding precautionary measures. Endotoxins in humans and animals can lead to sepsis, to a strong incorrect response of the immune system. Hence, for example when producing pharmaproteins, contamination with endotoxin should be detected precisely and should be removed completely subsequently. Endotoxin represents a problem with genetically engineered pharmaceuticals, gene therapeutics or substances, which are injected into humans or animals (e.g. veterinary treatment or in animal tests). However, not only in medicinal but also in research applications, such as transfection experiments of mammal cells, inhibition or lowering of the transfection efficiency by means of endotoxin can be observed.

In order to be able to use proteins within the framework of clinical studies, the European and American pharmacopoeia demand that the proteins fall below specific boundary values for endotoxin level (e.g. immune serum globulin 0.91 EU/ml, this corresponds to 5 EU/kg bodyweight and hour (dosage=EU/kg*h); EU=endotoxin unit; FDA (Food and Drug Administration): Guideline on Validation of LAL as End Product). If a medicine or proteins contained therein have too high an endotoxin level, this can lead to the death of the experimentee. The misdirected immune defence damages the patient due to overreaction. This can lead to tissue inflammation, drop in blood pressure, heart racing, thrombosis, shock etc. Even a longer enduring endotoxin exposition in picogram quantities can lead to chronic side effects, such as e.g. immune deficiences, septic symptoms etc. Within the framework of substance production, in particular in processes with "good manufacturing practice" (GMP) conditions, it is therefore attempted to deplete endotoxin as far as possible. However, endotoxin removal in proteins, polysaccharides and DNA is problematic. In the case of proteins themselves, there are large problems due to their intrinsic properties, such as charge state or hydrophobicity, which can virtually prevent endotoxin removal or can lead to large product losses in the removal procedure.

At present, only three methods for endotoxin detection in biological solutions are described, only the first two methods being permitted by the FDA. 1. "Rabbit Pyrogen Testing"; a method in which a living rabbit is injected with an endotoxin solution and hence an immune reaction is triggered. This endotoxin-induced immune response is detected by the development of fever. 2. The "Limulus Amoebocyte Lysate (LAL) "-Test, the test which is used most frequently at present (Bio Whittacker, Inc., Charles-River, Inc., Associates of Cape Cod, Inc., all USA), can be standardised in a significantly improved way. With this method, the agglomeration of the blood of the horseshoe crab (Limulus polyphemus) is measured after endotoxin contact. 3. A further possibility is the use of a special cell culture system (Sterogene Inc., USA) with which activation of monocytes is tracked via the appearance of specific cytokines.

The two first-mentioned methods are however very expensive (cf. Competitive comparison endotoxin detection) and, due to the large requirement for test animals or for blood of the very rare horseshoe crab, are dubious not least on the grounds of animal protection. The LAL test can in fact also be miniaturised and automated but, due to low stability of the components, has huge disadvantages in application. Once a LAL solution has been opened it must be processed and used up immediately since the components aggregate within a few hours. Skilled personnel are required for all test methods and the methods are very susceptible to interference, because for example the immune system of rabbits can react entirely differently to the same dose of endotoxin. The cell culture method of the Sterogene Company, like all cell culture methods, is likewise very complex and has problems with respect to standardisation.

It can be established overall that there is no easily handled economical method for endotoxin detection and the methods used at present have a series of disadvantages. There is therefore a requirement for a method which avoids these disadvantages.

There is in general a series of methods for endotoxin depletion from biological solutions. Particularly in the case of proteins, there have however to date been no generally applicable standard methods. The respectively used methods are adapted to the specific properties of the respective protein and to the corresponding production process of the protein. There are various possibilities for endotoxin depletion, each of these methods having specific advantages and disadvantages.

Ultrafiltration (Petsch, D. & Anspach, F. B., 2000, J. Biotechnol. 76, 97-119 and references therein) is used for endotoxin depletions from water and solutions with low-molecular components, such as salts, sugars and antibiotics but is not suitable for high-molecular proteins or DNA.

2-phase extraction (e.g. WO 0166718, Merck) is intended to separate water-soluble proteins and DNA from endotoxin but produces detergent residues in the purified product. The method is in addition time-consuming due to multiple repetition of the purification procedure.

An anion exchanger (DEAE) method is used likewise for endotoxin depletion from DNA and basic proteins (e.g. U.S. Pat. No. 5,990,301, Qiagen; WO 9414837, Enzon) but requires a low ionic strength (<50 mM NaCl) and leads to a protein co-adsorption in the case of acidic proteins.

A further method for endotoxin depletion from DNA and proteins (e.g. BSA, myoglobin, gamma-globulin, cytochrome C) is affinity-adsorption (e.g. polymyxin B, histamine, histidine, polylysine) e.g. GB 2192633 (Hammersmith Hospital) which is however toxic in the case of polymyxin B and can lead to co-adsorption of proteins in the case of low ionic strengths.

Furthermore, immune-affinity-chromatography is used, the specificity for specific endotoxins being able to be achieved only via expensive antibodies (U.S. Pat. No. 5,179,018, Centocor; WO 0008463, Bioserv) against core oligosaccharide.

Furthermore, the S3delta-peptide (WO 0127289) of the factor C (a component of the LAL test) (WO 9915676, both: National University of Singapore) is used with proteins (e.g. BSA, chymotrypsinogen), this method having however low efficiency in the case of high ionic strengths and high production costs are also involved (production in insect cell culture).

In application in the pharmaceutical industry, essentially three methods are found for protein solutions adapted to the properties of the target proteins;

anion exchanger chromatography reversed-phase chromatography; this has the disadvantage that it is not equally suitable for all proteins—in particular is problematic in the case of hydrophobic proteins. This method is furthermore very time-consuming.

Rem Tox (Millipore Company): this method has the disadvantage that, in addition to a very long incubation duration, the non-specific binding component is high and the protein retrieval is often not adequate.

A rough endotoxin depletion of proteins to a value up to 10 EU/ml is possible in many cases with the existing methods. The remaining concentration of endotoxin however always still has a toxic effect. A further depletion (=fine purification) is therefore offered or, dependent upon the dose of the protein in the medical application, is prescribed as mandatory by the European pharmacopoeia (e.g. 5 EU/kg bodyweight and hour in intravenous applications) and by the FDA. However, this fine purification is often not ensured satisfactorily with present methods. The current market methods have here significant disadvantages and, in the case of specific proteins, often cannot be applied or only with considerable losses of the target protein.

The object underlying the invention is therefore to provide a method which can detect endotoxins in samples. Furthermore, the object underlying the invention is to provide a method with which endotoxins can be removed from aqueous solutions.

The objects are achieved by the subject defined in the patent claims.

The subsequent Figures explain the invention.

FIG. 1 shows a schematic overview of the chemical structure of endotoxin from E. coli O111:B4. Hep=L-glycero-D-mannoheptose; Gal=galactose; Glc=glucose; KDO=2-keto-3-deoxyoctonate; NGa=N-acetyl-galactosamine; NGc=N-acetylglucosamine.

Figure 2:
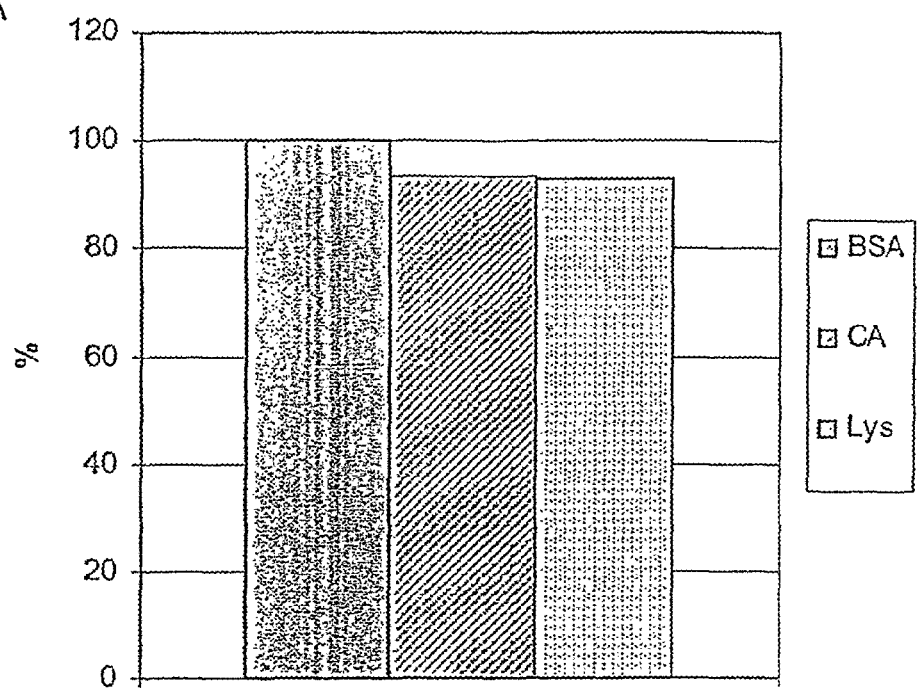
Figure 2:
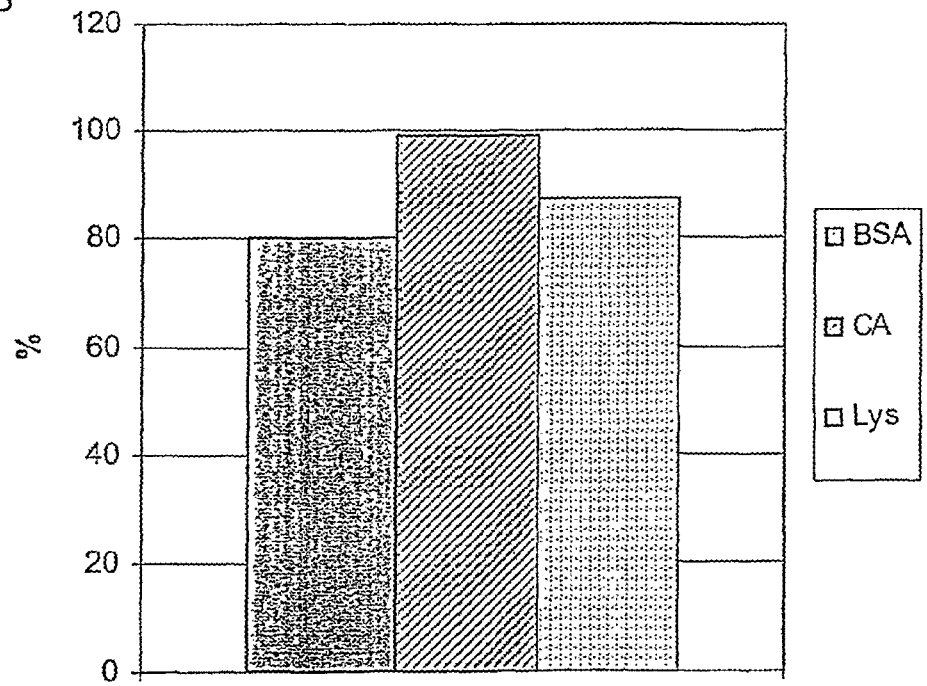

FIG. 2 shows the results of tests with chromatography columns which carry NStrepS3Cp12 immobilised via sulfhydryl radicals. (A) Endotoxin removal from protein solutions: bovine serum albumin (BSA), carbonic anhydrase (CA) and lysozyme (Lys) were incubated for 1 h on the column and subsequently eluted with buffer. The endotoxin concentration before and after the column was measured with the LAL test and the percentage removal was calculated therefrom. (B) Protein retrieval: the protein concentrations of the starter solutions and the fractions after the column were determined by absorption measurement at 280 nm and the percentage protein retrieval was determined therefrom.

Figure 3:
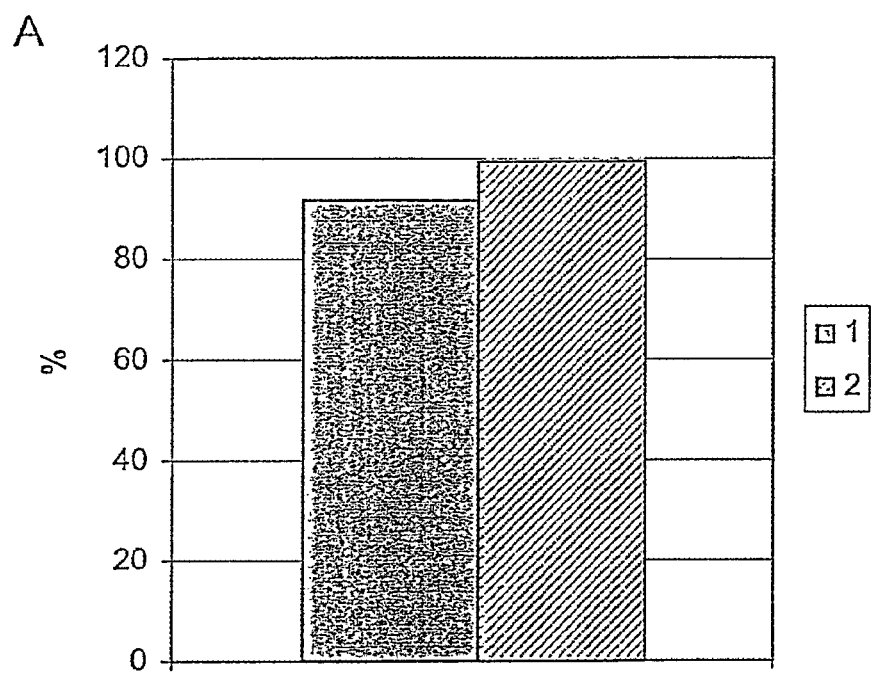
Figure 3:
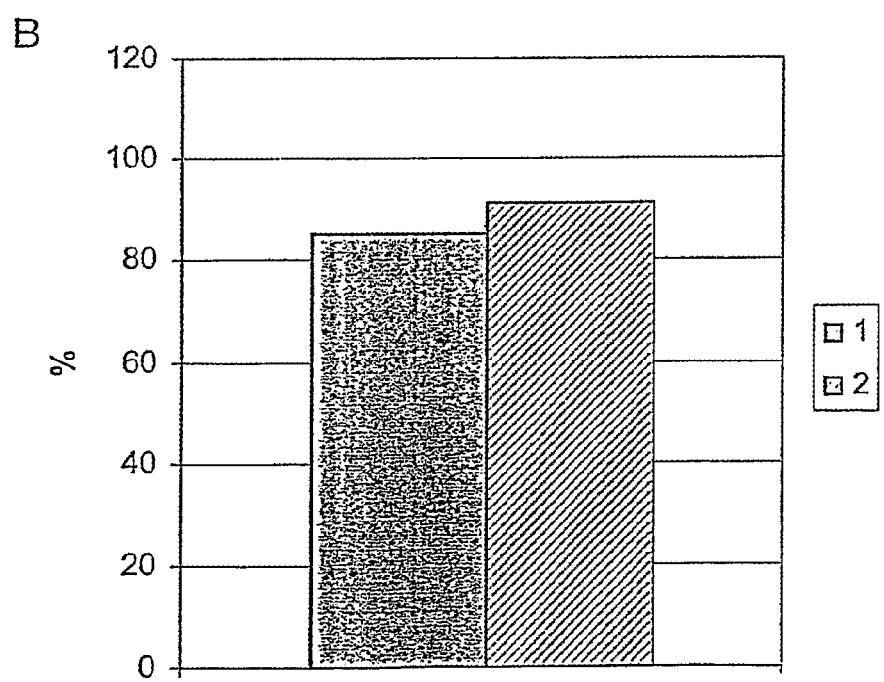

FIG. 3 shows the endotoxin removal from a lysozyme solution via chromatography columns with "undirected" (1) and "directed" (2) immobilised p12. In both cases, p12S3C was bonded to NHS-activated columns. The "undirected" immobilisation was effected via primary amino radicals of p12S3C, which produce covalent compounds with the carrier substance by reaction with the NHS groups. A "directed" cross-linking of p12S3C via an N-terminal cysteine is achieved by diamino ethane and SIA (N-succinimidyl-iodoacetate). (A) Percentage endotoxin removal. (B) Protein retrieval.

Figure 4:
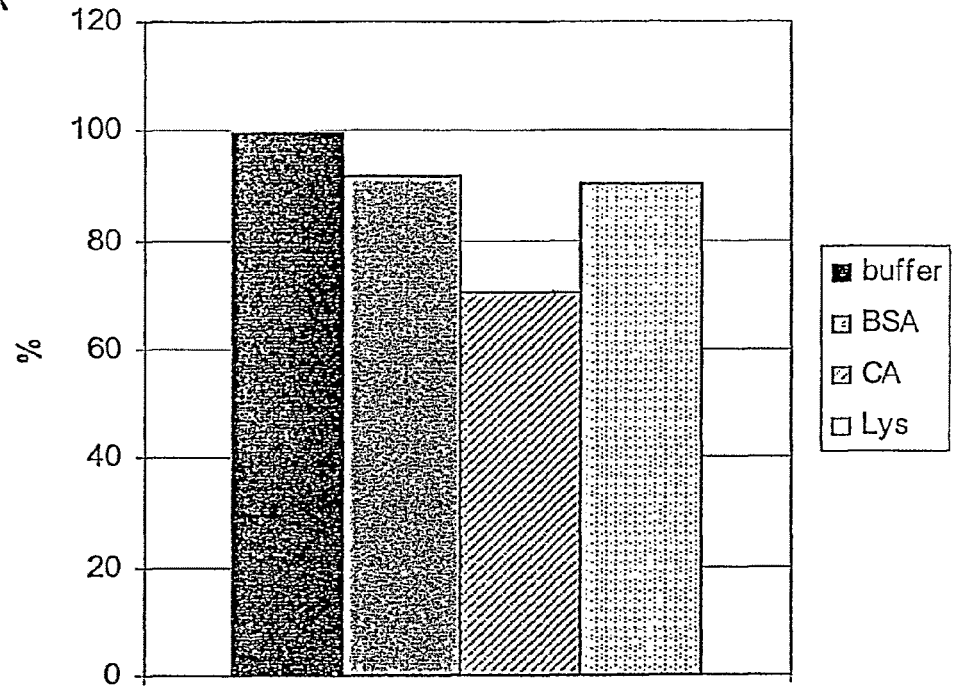
Figure 4:
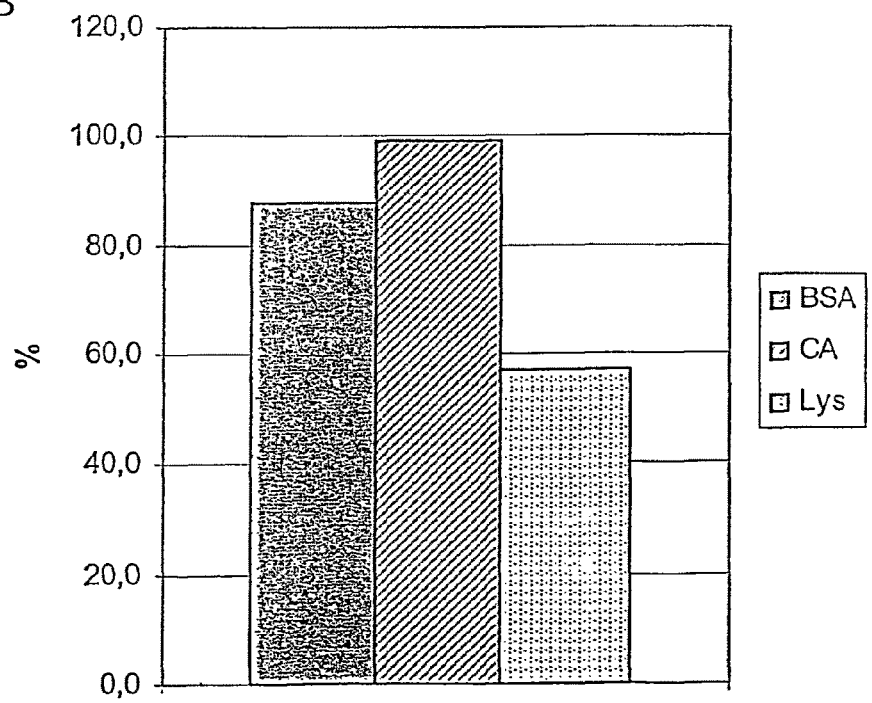

FIG. 4 shows the results of tests with biotinylated p12 which was bonded to magnetic beads via streptavidin. (A) Endotoxin depletion from buffer (20 mM hepes, 150 mM NaCl, pH 7.5) and protein solutions was determined by means of LAL test. (B) The protein retrieval was determined for the protein solutions by absorption measurements. The separation of the beads from the solution was effected by means of a magnet separator. BSA: bovine serum albumin. CA: carbonic anhydrase. Lys: lysozyme.

Figure 5:
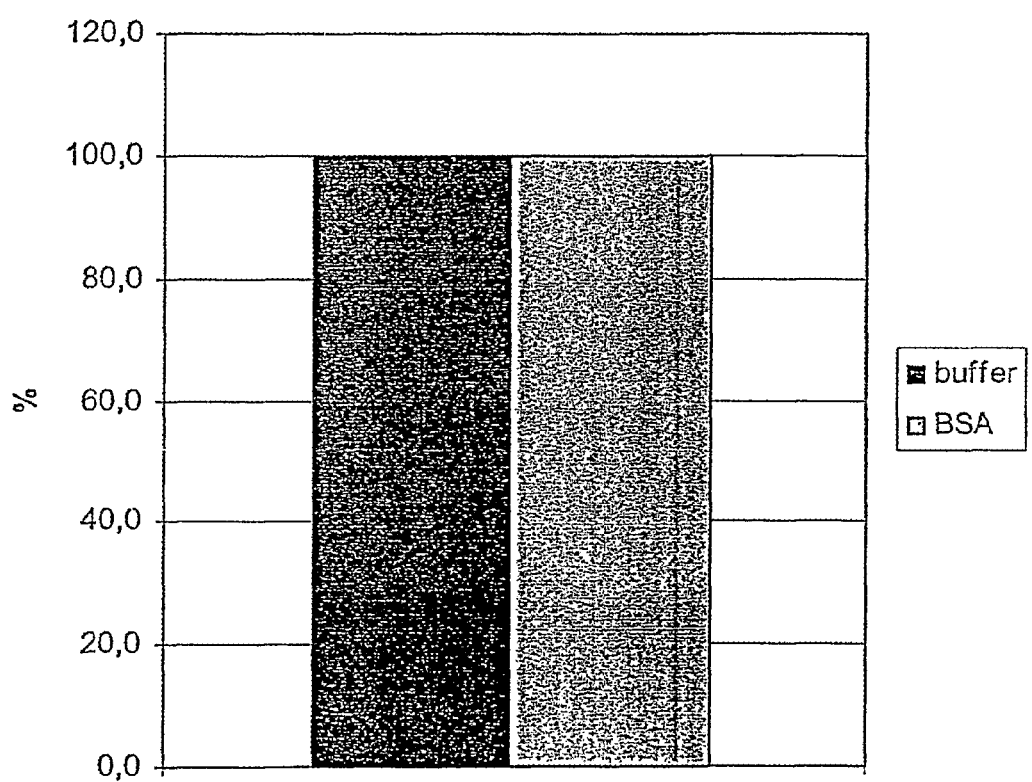

FIG. 5 shows the results of the endotoxin removal with p12 which was immobilised on agarose beads via biotin-streptavidin interactions. The separation of the immobilised p12 was effected by centrifugation. The endotoxin removal from buffer (20 mM tris, 150 mM NaCl, pH 8.0) and BSA solutions was determined by means of the endotoxin concentrations of starter solution and residue.

Figure 6:
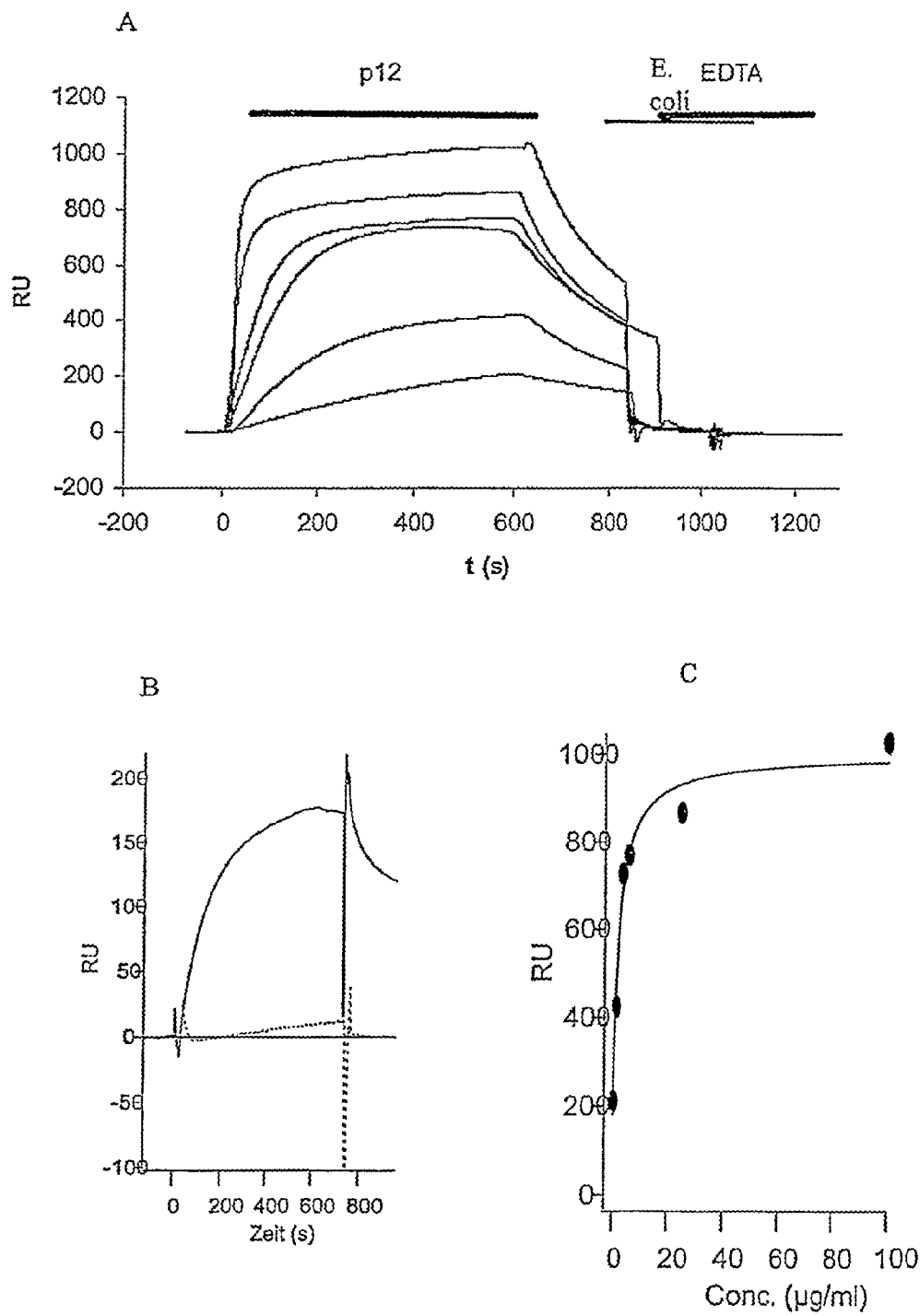

FIG. 6 shows results of surface-plasmon-resonance measurements. (A) Resonance curves which were measured as response to injection of various (respectively in μg/ml: 100; 25; 6.25; 4; 1.56; 0.4) p12 concentrations (_____). Binding is effected on endotoxin from E. coli D21f1 which was immobilised on a hydrophobic HPA chip. The injection of p12 and EDTA (5 mM) is marked via bars over the curves. Buffer: 20 mM tris, 150 mM NaCl, pH 8.0. (B) Equilibrium resonance values for the binding of p12 to immobilised endotoxin were measured approximately 600 s after the beginning of the p12 injection and plotted against the associated p12 concentration. The continuous line shows a fit of the Langmuir adsorption isotherms ($RU=RU_{max}*[p12]/[p12]+K_d$)) to the data. (C) Binding of E. coli to biotinylated p12 which was immobilised on streptavidin chips. E. coli D21e8 (_____), the inner core region of which is complete, to p12. In contrast, E. coli D21f2 (_____), which has a greatly shortened core region, does not bind to p12. The measurements were implemented in PBS.

FIG. 7 shows schematically the structure of the endotoxin core region of various E. coli mutants.

Figure 8:
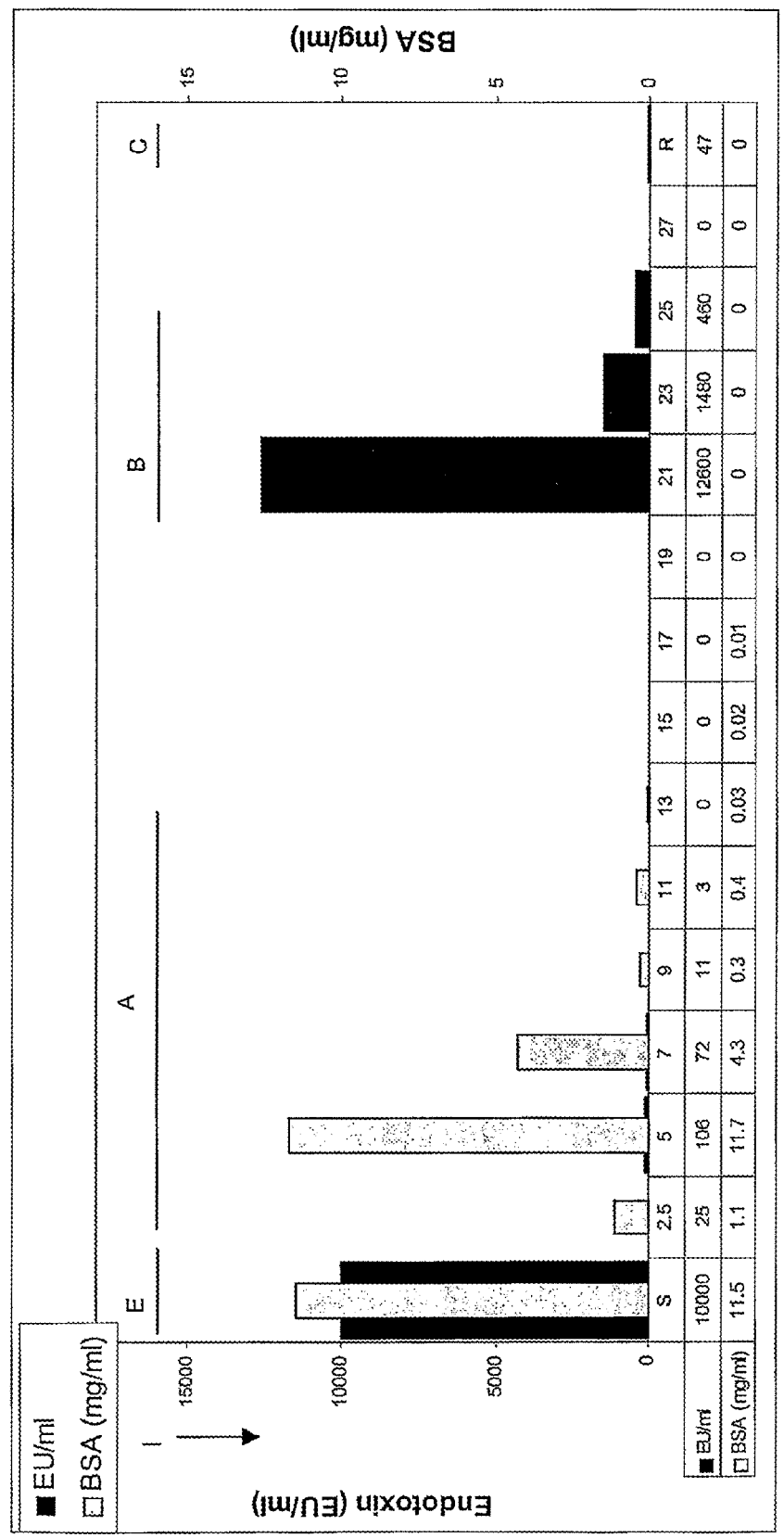

FIG. 8 shows schematically the result of an endotoxin depletion by means of chromatography column throughflow methods. E means equilibration buffer (20 mM hepes, 150 mM NaCl, 0.1 mM $CaCl_2$, pH 7.5), A means washing buffer A (20 mM hepes, 150 mM NaCl, 0.1 mM $CaCl_2$, pH 7.5), B means elution buffer B (20 mM hepes, 150 mM NaCl, 2 mM EDTA, pH 7.5), C means regeneration buffer C (20 mM hepes, 150 mM NaCl, 2 mM EDTA, 0.005% NaDOC, pH 7.5), S means concentration of protein and endotoxin in the starter solution. BSA means bovine serum albumin. EU means endotoxin units. After injection (I) of 4 ml of the starter solution (S), re-rinsing took place with 15 ml washing buffer and the throughflow was fractionated (respectively 2.5 ml during application, respectively 2 ml during washing). Subsequently, the column was regenerated with the buffers B and C and the discharge was collected likewise in fractions (respectively 2 ml). As is evident in the Figure, the BSA could be found in the first 3-5 fractions after the injection. The content of endotoxin in these fractions was lower by the factor 100 than in the starter solution. The endotoxin bonded to the column was then washed from the column with the buffers B and C.

Figure 9:
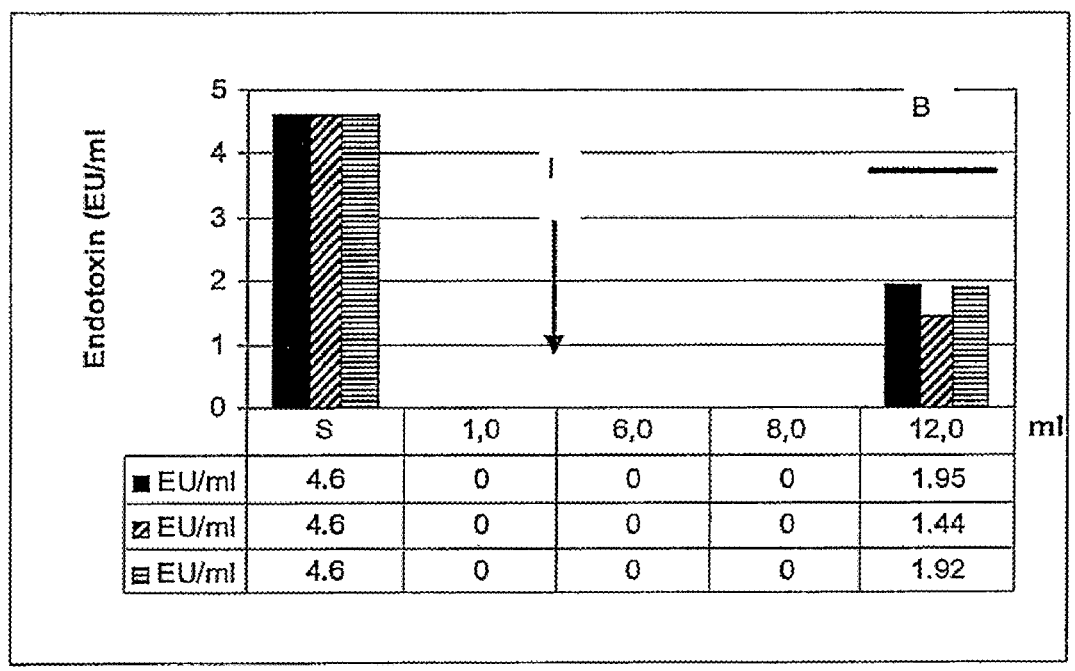

FIG. 9 shows schematically the results of the endotoxin removal from slightly contaminated buffer solution (5 EU/ml) in the throughflow method. p12 was immobilised (8 mg p12/1 ml sepharose), undirected towards NHS-activated sepharose 4 FastFlow (Amersham Biosciences, Uppsala, Sweden) and 3 columns were filled with respectively 2 ml column volumes. The experiment was implemented in parallel on 3 columns. Prior to the application of the sample, respectively 1 ml equilibration buffer (20 mM hepes, 150 mM NaCl, 0.1 mM $CaCl_2$, pH 7.5) was collected, thereafter the sample (S: endotoxin from *E. coli* O55:B5 in equilibration buffer, 4.6 EU/ml) was injected (I) and the fractions of 5 ml and 2 ml were collected. The regeneration of the column was effected by the addition of 4 ml regeneration buffer (B: 20 mM hepes, 150 mM NaCl, 2 mM EDTA, 0.005% NaDOC, pH 7.5). The endotoxin concentration was determined by means of the LAL test (kinetically chromogenic LAL test, Charles-River Inc.). The endotoxin impurities were able to be removed completely in all three experiments, i.e. the endotoxin concentration in the throughflow was below the detection limit (<0.005 EU/ml).

The term "endotoxin depletion" as used here means complete or partial removal of endotoxin from sample material.

The term "endotoxin" as used here describes bacterial lipopolysaccharide which is a component of the outer membrane of Gram-negative bacteria.

The term "bacteriophage tail protein" as used here describes those proteins which occur in bacteriophages and can bind components of cell membranes. Normally, these proteins are localised in the bacteriophage tail but can also be localised on the bacteriophage head or on the normal bacterial shell in the case of bacteriophages without a tail. The cell components bonded by the bacteriophage tail protein detect in particular endotoxins.

The term "non-specific immobilisation" or "undirected immobilisation" as used here means that coupling of a protein to a matrix is effected via protein radicals (primary amines) which are distributed over the entire protein surface. The choice of group used for the coupling of the individual protein molecule is random.

The term "directed immobilisation" as used here means that coupling is effected via amino acid radicals or other radicals (e.g. glycosylations of the protein), the position of which in the protein (e.g. N- or C-terminal) is known. The choice of these groups for the coupling is effected by the choice of suitable reaction partners/linkers which react preferably with these radicals (e.g. coupling of sulfhydryl radicals to iodoacetate radicals; iodoacetate reacts a thousand times more quickly with sulfhydryl radicals than with amino radicals).

The present invention relates to a method for detecting endotoxin, comprising the steps:
a) incubation of a sample with a bacteriophage tail protein,
b) detection of endotoxin bonded to bacteriophage tail proteins.

The invention relates preferably to a method, in which the detection is implemented by means of spectroscopic methods, e.g. fluorescence emission, fluorescence polarisation, absorption or circular dichroism, or by means of capacitance measurement, e.g. electrical signals or indirectly by means of competition detection.

If necessary, after step a) and before step b), an additional step a'), separation of bacteriophage tail protein-endotoxin complex from the sample, is introduced.

The present invention relates furthermore to a method for removing endotoxin from a sample, comprising the steps:
a) incubation of a sample with or bringing a sample into contact with bacteriophage tail proteins which are immobilised on a fixed carrier, in a non-specific or directed manner,
b) separation of the bacteriophage tail protein-endotoxin complex from the sample.

Preferably, the ion composition of the bivalent ions, e.g. $Ca^{2+}$, $Mg^{2+}$ and/or the pH value is adjusted before incubation in order to obtain an optimal endotoxin-bacteriophage tail protein binding. Furthermore, during or after incubation, "demasking" of the bonded endotoxin by addition of detergents and/or salts, e.g. Tween, triton NaCl or ammonium sulphate or other substances, e.g. chitosan, sugar or lipids, which accelerate detachment of the endotoxins from e.g. proteins or nucleic acids, is preferred.

The bacteriophage tail protein can be naturally occurring or be molecular-biologically or biochemically modified. The bacteriophage tail protein can be modified by genetic engineering and/or biochemically for various reasons. For the methods according to the invention, not only the naturally occurring bacteriophage tail proteins can however be used, but also their variants. In the sense of the present invention, variants means that the bacteriophage tail proteins have an altered amino acid sequence. These can be obtained by screening of the naturally occurring variants or by random mutagenesis or targeted mutagenesis, but also by chemical modification. The bacteriophage tail proteins used for the methods according to the invention can be adapted by targeted or random mutagenesis in their specificity or their binding properties to carrier structures. This binding to the carriers can be effected permanently, e.g. covalently or via a specific or non-specific biotinylation, but also can be effected reversibly, e.g. via a reducible disulfide bridge. Furthermore, the stability can be increased by a modification. By means of the molecular-biological or chemical mutagenesis, mutations are introduced which can be amino acid additions, -deletions, -substitutions or chemical modifications. These mutations can effect a change in the amino acid sequence in the binding region of the bacteriophage tail proteins, with the aim of adapting specificity and binding affinity to test requirements, e.g. increasing the binding of the endotoxins to the bacteriophage tail proteins or making them irreversible in order to improve detection or depletion. Furthermore, a genetically engineered or biochemical modification of the phage proteins can be implemented with the aim of switching off the possibly present enzymatic activity in order consequently to improve the binding or to make it irreversible. Furthermore, a genetically engineered or chemical modification of the phage proteins can be implemented in order to adapt the present physical properties of the protein, such as solubility, thermal stability etc., in the sense of the method according to the invention.

Work to explain the three-dimensional structure of T4 p12 had shown that, at increased temperature, proteolytic fragments of 33 kDa and 45 kDa can be produced, the N- and C-terminal (33 kDa) or only N-terminal (45 kDa) are shortened. In contrast to the 33 kDa fragment, the 45 kDa fragment is still able to bind to bacteria. Consequently, the C-terminus is involved in the cell binding.

The modification can furthermore have the purpose in particular of enabling direct detection, e.g. by means of measurement of the tryptophan fluorescence. For example p12 has five tryptophan radicals. The fluorescence spectrum of the native protein indicates that these radicals are extensively solvent-inaccessible. It is known from a multiplicity of scientific works that aromatic amino acids are almost always involved in the binding of sugar radicals, as occur also in endotoxin. The binding of the sugar radicals to proteins can be followed by a quench of the tryptophan fluorescence or if necessary also in addition by changing the fluorescence maximum. It can be supposed from some works that the unfavourable distribution of the fluorophores of natural p12 prevents exploitation of the fluorescent properties of p12 for binding measurement. The fluorescence properties of p12 are dominated by the five tryptophan radicals, the fluorescence of which is altered by the addition of endotoxin in a non-measurable manner. It is expected from these data that rather tyrosine radicals are involved as tryptophan radicals in the binding, the signal alteration of which cannot be made visible in front of the high tryptophan background. On the basis of the proteolysis results, six tyrosines on the C-terminus of p12 are possible for the endotoxin detection kit which can be made correspondingly "visible". By means of a selective molecular-biological exchange of the five tryptophan radicals for tyrosines, the spectroscopic properties are specifically altered in a first step such that the endotoxin binding by fluorescence signal alteration of a single tryptophan radical is measurable. Subsequently, by means of a specific exchange of respectively one of the six tyrosines in the C-terminal region for a tryptophan radical, the intensity of the measurable signal is significantly increased in order to obtain attractive signal differences for the development of an endotoxin-detection kit.

The bacteriophage tail proteins which are used depends upon which endotoxins are intended to be detected or drawn off. Even now, a large number of known bacteriophages is available for a large part of the previously described bacteria and can be used for the methods according to the invention. The phages and the corresponding host bacteria are inter alia obtainable in the case of the following strain collections: ATCC (ISA), DSMZ (Germany), UKNCC (Great Britain), NCCB (Netherlands) and MAFF (Japan).

Preferably, the bacteriophage tail proteins for the methods according to the invention stem from bacteriophages, the host bacteria of which have relevant significance with respect to medicine or biotechnology, such as e.g. *E. coli* which is used in the production of recombinant proteins or of nucleic acids for gene therapy. The bacteriophage tail proteins which bind highly conserved regions of endotoxin, such as e.g. the core region or lipid A, are particularly preferred. In particular, p12 and p12-similar bacteriophage tail proteins are preferred. In a combination of endotoxin impurities from various host bacteria, a combination of the corresponding endotoxin-detecting bacteriophage tail proteins can be used.

The detection or the depletion of endotoxin in or from a sample is effected via the binding of endotoxin to the bacteriophage tail proteins. This binding can be detected for example by direct measurement by means of spectroscopic methods, e.g. via fluorescence emission, fluorescence polarisation, absorption or circular dichroism. Furthermore, the binding can be made visible by electrical signals, e.g. a capacitance measurement. Furthermore, the binding of endotoxin to the bacteriophage tail proteins can also be detected indirectly via displacement experiments.

For the detection according to the invention, the bacteriophage tail proteins, if separation of the bacteriophage tail protein-endotoxin complexes from the sample is required, can be coupled to suitable carrier structures, e.g. magnetic particles, agarose particles, microtitre plates, filter materials or throughflow cell chambers (indirect detection). The carrier structures can comprise for example polystyrene, polypropylene, polycarbonate, PMMA, cellulose acetate, nitrocellulose, glass, silicon or agarose. The coupling can be achieved for example by adsorption or covalent binding.

For the depletion method according to the invention, the bacteriophage tail proteins are coupled to permanent carriers. The permanent carriers can be materials for chromatography columns (e.g. sepharose materials), filtration media, glass particles, magnetic particles, centrifugation- or sedimentation materials (e.g. agarose particles).

Functional coupling is hereby important, i.e. bacteriophage tail proteins, despite binding to the carrier material, have structures which are accessible for endotoxin. The coupling of the bacteriophage tail proteins can be effected non-specifically or else preferably directed, via for example a selective biotinylation or coupled or via a spacer or linker.

For this purpose, the bacteriophage tail proteins can be cross-linked with low-molecular substances, e.g. biotin, in order to bind via these low-molecular substances to polypeptides, e.g. streptavidin, which for their part were immobilised on the carrier. Instead of biotin, the so-called Strep-tag (Skerra, A. & Schmidt, T. G. M. Biomolecular Engineering 16 (1999), 79-86) can furthermore be used, which is a short amino acid sequence and binds to streptavidin. Furthermore, the His-tag can be used which, via bivalent ions (zinc or nickel) or an antibody specific for it (Qiagen GmbH, Hilden), can bind to a carrier material. The Strep-tag and the His-tag are bonded preferably via DNA recombination technology to the recombinantly produced bacteriophage proteins. This coupling can be effected directed, e.g. on the N- or C-terminus or be undirected. The directed coupling is effected via a suitable, reactive amino acid, such as cysteine, which is of course not frequently surface-exposed in phage proteins and has been introduced specifically at a suitable position. Since phage tail proteins are synthesised in the cytoplasma, disulfide bridges do not need to be taken into account. Preferably, coupling can take place also via other amino acids, directly or as also with cysteine indirectly via a "spacer" or "cross linker" (monofunctional or bifunctional).

In the case of cysteine coupling, all bifunctional crosslinkers with NH- and SH-reactive groups are possible, with and without intermediate spacers, e.g. 11-maleimidoundecanoic acid sulfo-NHS or succinimidyl-4-[N-maleimidomethyl]-cyclohexane-1-carboxy-[6-amido]caproate. If no spacers are present, 8-12 C-atom-spacers with a terminal NH group can be inserted. Preferably the cysteine coupling is effected via a specific biotinylation of cysteine by for example EZ-link-PEO-maleimide activated biotin (Pierce).

Bivalent ions, such as e.g. $Ca^{2+}$ or $Mg^{2+}$ are important for binding endotoxins to phage proteins, such as p12. By adding suitable chelating agents, such as e.g. EDTA or EGTA, this binding can however be broken. For the binding, $Ca^{2+}$ concentrations are preferred in the range of approximately 0.1 µM to approximately 100 mM, particularly preferred in the range of approximately 0.1 µM to approximately 10 mM, and especially preferred in the range of approximately 0.1 µM to approximately 1 mM and furthermore particularly preferred in the range of approximately 10 µM to 1 mM. If the concentration of bivalent ions is lowered by adding 1 mM EDTA under 100 nM, then the binding of endotoxin to p12 is broken. $Mg^{2+}$ concentrations above 10 mM make the binding of endotoxin to p12 worse, which becomes noticeable in an increase in the dissociation constant. Without addition of $Mg^+$, a $K_d$ value of 50 nM is produced and, in a buffer with 10 mM $Mg^{2+}$, a $K_d$ value of 1 µM was measured. Zinc revealed an even higher inhibiting effect. 1 mM Zn increases the $K_d$ value to 10 µM. An adjustment of the concentration of bivalent or other ions (e.g.: $Cu^{2+}$, $Al^{3+}$, $Zn^{2+}$, $Fe^{2+}$, $Ca^{2+}$, $Ba^{2+}$, $Mg^{2+}$, $Cd^{2+}$) to a range which is optimal for the binding, can be effected by substances such as HEDTA, NTA or general chelating agents/buffers (ADA: N-[2-acetamido]-2-iminodiacetic acid; 5-AMP: adenosine-5'-monophosphate; ADP: adenosine-5'-diphosphate; ATP: adenosine-5'-triphosphate; Bapta: 1,2-bis(2-aminophenoxy)ethane-N,N,N',N',-tetraacetic acid; citrate: citric acid; EDTA: ethylene diamine tetraacetic acid; EGTA: ethyleneglycol-bis(β-aminoethyl ether) N,N,N',N'-tetraacetic acid; HEDTA: N-hydroxyethylethylenediaminetriacetic acid; NTA: nitrilotriacetic acid; $SO_4$ sulfate), which can be used as buffers for bivalent ions.

The methods according to the invention can therefore comprise further washing steps. According to whether a direct or indirect detection or the depletion requires separation of sample and bacteriophage tail protein, washing steps can be incorporated. Since $Ca^{2+}$ or other metal ions (e.g. $Mg^{2+}$) are essential for the binding, the binding of endotoxin to e.g. p12 can be broken by suitable washing steps. According to the aim of whether endotoxin is intended to remain bonded on the bacteriophage tail protein, e.g. p12, washing takes place with EDTA-free buffer, if the binding is intended to be broken, with EDTA-containing buffer, the EDTA concentrations being in the range of at least 0.05 mM to more than 10 mM, preferably in the range of 2 mM to 5 mM.

The separation is effected after incubation of the sample with the carrier material, which is coupled correspondingly with bacteriophage tail proteins, for approximately 5-60 min or approximately 30-180 min or, if required, also overnight. For this purpose, the sample is eluted e.g. from the chromatography column, or filtered or the corresponding particles are centrifuged off or sedimented off or are separated magnetically by applying a magnetic field. The separation in the batch method described here, i.e. with pre-incubation of sample and carrier materials, which are coupled with the corresponding bacteriophage tail proteins, can be sensible in particular with very low endotoxin concentrations.

The depletion of endotoxins via chromatography columns can however also be effected in the pure throughflow method. The sample can be applied to the column for this purpose, which column contains a carrier material with bacteriophage tail proteins coupled thereto. The flow rate is dependent upon the volume and geometry of the column. The flow rate is furthermore dependent upon the volume and endotoxin content of the sample in order to achieve, by means of as long a contact time as possible between column and endotoxin, even in the case of low endotoxin concentrations, an efficient depletion. The contact time is thereby the time which the sample requires from application on the column until flowing out.

The separation step can be used for example in the depletion method to regenerate the bacteriophage tail proteins which are coupled to the permanent carrier. As a result, the permanent carrier, e.g. a matrix, can be recycled in a chromatography column. Regeneration is effected by removing the bonded endotoxin by means of a suitable regeneration buffer containing EDTA or a corresponding chelating agent. In the case of EDTA, a concentration of greater than 2 mM EDTA is preferred, in particular greater than 10 mM EDTA.

Since ionic interactions can fundamentally always be affected by changes in the ion strength, increases or reductions of other salts in the solution, such as e.g. NaCl or KCl, can also affect the binding of endotoxin to the bacteriophage tail proteins.

In order to make the binding visible directly or indirectly in the detection method, the protein can also be altered molecular-biologically or biochemically in order to enable measurement or to improve it. In order to make binding of endotoxin e.g. to p12 directly visible, a molecular-biological exchange of tyrosine radicals for tryptophan can be implemented. It can thereby be necessary for a reduction in the signal background to exchange the originally contained tryptophans for tyrosines. In order to be able to make measurements also in protein-containing solutions, p12 can be modified chemically in addition after tryptophan introduction. Tryptophan radicals are thereby altered by Koshland reagent (2-hydroxy-5-nitrobenzylbromide) with respect to their spectroscopic properties. In the case of displacement experiments, marked, e.g. fluorescence-marked endotoxin (e.g. Sigma) can be displaced by endotoxin, e.g. by p12, which is located in the sample and the concentration of free fluorescent endotoxin can be determined.

With the method according to the invention, endotoxin can be detected in and removed from all aqueous solutions. These solutions can contain: proteins, plasmid-DNA, genomic DNA, RNA, protein-nucleic acid complexes, such as e.g. phages or viruses, saccharides, vaccines, drugs, dialysis buffers (medicine), salts or other substances contaminated by endotoxin binding.

A further aspect of the invention is bacteriophage proteins, to which the so-called tags, e.g. the Strep- or His-tag, are coupled preferably to the N- or C-terminus of the protein, particularly preferred to the C-terminus. The coupling or cross-linking of the tags with the bacteriophage proteins via DNA recombination technology is preferred. Production of the nucleic acid, comprising the sequence of the bacteriophage protein and of the tag and the production of the expression product are the state of the art and do not require to be explained here separately. A further aspect of the invention is the nucleic acid sequence which encodes a bacteriophage protein together with the Strep- or His-tag. The p12 protein of the phage T4 is a particularly preferred bacteriophage protein which is modified with the Strep- or His-tag but all other bacteriophage proteins, which are involved in detection and binding of bacteria or are responsible for this, are likewise preferred.

A further aspect of the invention is bacteriophage proteins with a tag which has a surface-exposed cysteine for specific directed biotinylation, e.g. the tags according to SEQ ID NO: 5, 6 and 7. An example of a p12 with a tag is the amino acid sequence cited in SEQ ID NO: 8. A p12 with a tag is preferred, in particular a p12 with a tag with a surface-exposed cysteine, in particular a p12 with the tag according to SEQ ID NO: 6 and 7. This directed biotinylation can be imparted in addition by a suitable spacer or linker. Furthermore, the present invention relates to the amino acids with a sequence according to SEQ ID NO: 5, 6 and 7. Furthermore, the present invention relates to the nucleic acids which encode the amino acid sequence according to SEQ ID NO: 5, 6 and 7.

The methods according to the invention, relative to detection and purification methods for and of endotoxin, offer advantages in the performance of corresponding applications. Furthermore, the production of antibodies against LPS core oligosaccharides is very difficult, which renders corresponding methods based on antibodies very expensive.

The following examples explain the invention and should not be understood as restrictive. If not otherwise indicated, molecular-biological standard methods were used, such as e.g. described by Sambrook et al., 1989, Molecular cloning: A Laboratory Manual $2^{nd}$ edition, Cold Spring Harbor Laboratory Press, Cold Spring Harbor, N.Y.

1. Glass Vessels, Plastic Vessels and Buffers

For the endotoxin removal, all the glass vessels were depyrogenated by heating at 200° C. (4 h) and exclusively pyrogene-free plastic materials (e.g. pipette tips, microtitre plates) were used. Other non-heat resistant appliances or vessels were treated either with 3% hydrogen peroxide or washed with 1% sodium deoxycholate. Subsequently, they were rinsed with endotoxin-free water. The buffers were produced from extensively endotoxin-free buffer substances (Sigma) and mixed with endotoxin-free water. Salts, such as e.g. NaCl, which can be heated to 200° C., were heated up (200° C., 4 h). Buffers used for chromatographic purifications were degassed and filtered.

2. Endotoxin Detection by Means of LAL Test

Endotoxin control tests were implemented with a chromogenic LAL test (Limulus-Amoebocyte-Lysate test, Charles-River Endosafe, Charleston, USA) corresponding to the instructions of the producer. In order to determine the concentrations, endotoxin standards (Charles-River Endosafe, Charleston, USA) in the range of 0.005-50 or 0.02-50 EU/ml were used. The absorption measurement at 405 nm took place in a temperature-controlled microtitre plate reader (Genios, Tecan GmbH).

3. Western-Blot for p12 Detection

The detection of p12 in the residue of samples treated with beads or in the fractions of the affinity chromatography was effected by Western Blots. In part, the proteins were concentrated in advance by NaDOC/TCA precipitation (sodium deoxycholate/tetrachloroacetate). The samples were electrophoretically separated for this purpose on 12% SDS gels and transferred onto PVDF membranes (Immobilon, Millipore). The membranes were washed with PBS for 30 min, blocked with 5% milk powder (1 h) and subsequently incubated with polyclonal anti-p12 antibody (1 h, dilution: 1:1000). After incubation with a secondary antibody (goat-anti-rabbit IgG), conjugated with alkaline phosphatase, the development of the samples was effected with BCIP/NBT (5-bromo-4-chloroindolylphosphate/nitroblue tetrazolium salt).

4. Endotoxin Purification

The purification of endotoxin was implemented according to the specification of Galanos, C., Lüderitz, O. & Westphal, O. 1969, Europ. J. Biochem. 9,245-249.

Example 5

Specific Coupling of p12 to Immobilised Iodoacetyl Radicals

In order to achieve a directed binding of p12 to the surface, the amino acid serin at position 3 of the Strep-tag according to SEQ ID NO:5 was replaced by cysteine as in example 12 and the protein was immobilised via iodoacetyl radicals which bind preferably free sulfhydryl radicals. The resulting p12 was called p12S3C.

A 1 ml Sulfolink Coupling Gel (Pierce) was poured out, washed with 6 ml 1% sodium deoxycholate and equilibrated with 6 ml coupling buffer (50 mM tris, 150 mM NaCl, 5 mM EDTA, pH 8.5). Subsequently, 1 ml p12S3C (=N-strepS3Cp12) was injected (1-1.5 mg/ml in coupling buffer), the column was agitated gently for 15 min, incubated for a further 30 min without agitation at room temperature, and 1 ml p12S3C was injected again and the incubation steps were repeated. This coupling of p12S3C was repeated in total 4 times, and subsequently the column was washed with 6 ml coupling buffer. The throughflows were collected and the respective p12S3C concentration was determined by absorption measurement at 280 nm. 2.2-2.8 mg p12S3C per ml gel were bonded. Subsequently, surplus iodoacetyl radicals were blocked by incubation (45 min) with 1 ml cysteine (50 mM in 50 mM tris, 5 mM EDTA, pH 8.5). After washing the column with 16 ml 1M NaCl and 16 ml 20 mM hepes, 150 mM NaCl pH 7.5, the column was ready for use.

The capacity of this gel to remove endotoxin from protein solutions was tested with BSA (2-4 mg/ml), carbonic anhydrase (1-2 mg/ml) and lysozyme (3-4 mg/ml). BSA and lysozyme solutions were spiked with endotoxin from *E. coli* O55:B5 (Charles-River Endosafe, Charleston, USA) or *E. coli* HMS 174 (100-1000 EU/ml), whilst the carbonic anhydrase was not mixed with additional endotoxin. Respectively 0.5 ml protein solution was introduced to the column, incubated for 1 hour at room temperature and subsequently the column was washed with buffer. The proteins were collected in fractions and the endotoxin content, prior to and after the column, was determined by means of a chromogenic LAL test (Charles-River Endosafe, Charleston, USA). In addition, the protein retrieval was determined by absorption measurements at 280 nm. The endotoxins were able to be removed almost completely (93-99%) from all 3 protein solutions, as shown in FIG. 2A. In addition, the proteins were able to be eluted extensively from the column (80-99%, FIG. 2B). The column was finally regenerated with 5 mM EDTA, 20 mM hepes, 150 mM NaCl, pH 7.5. In order to exclude impurities of the protein fractions after running over the column due to separating p12, the fractions were tested for p12 by means of the Western Blot technique. No p12 was able to be detected in the fractions.

Example 6

Non-Specific Coupling of p12 to NHS-Activated Carrier Material

N-hydroxysuccinimide (NHS) is displaced from compounds by primary amino radicals and therefore is used to couple proteins to surfaces. NHS-activated sepharose columns (HiTrap NHS-activated HP, 1 ml, Amersham-Pharmacia-Biotech) were washed firstly with 6 ml ice cold 1 mM hydrochloric acid. Subsequently, 10-15 ml p12S3C (1.0-3.5 mg/ml) in 0.2 M NaHCO$_3$, 0.5 M NaCl, pH 8.3 were pumped in a circle over the column at room temperature (flow rate 0.8 ml/min). After 60 min, the throughflow was collected in fractions and the column was washed with 6 ml buffer. From these fractions, the NHS was separated by desalting the solution via HiTrap-desalting column (5 ml, Amersham-Pharmacia-Biotech) and subsequently the p12 quantity was determined by absorption measurement at 280 nm. 20-25 mg p12S3C were bonded to the column. The column was rinsed after the coupling corresponding to the instructions of the producer repeatedly with respectively 6 ml blocking buffer (0.5 M ethanolamine, 0.5 M NaCl, pH 8.3) and washing buffer (0.1 M acetate, 0.5 M NaCl, pH 4.0). Subsequently, the column was equilibrated with 6 ml usable buffer (20 mM hepes, 150 mM NaCl, pH 7.5 or 20 mM tris, 150 mM NaCl, pH 8.5).

The endotoxin removal via this column was tested with lysozyme solutions (3-4 mg/ml in 20 mM hepes, 150 mM NaCl, pH 7.5 or 20 mM tris, 150 mM NaCl, pH 8.5). The lysozyme solutions were spiked with endotoxin from *E. coli* HMS 174 (~500 EU/ml). 0.5 ml protein solution were introduced onto the column, incubated for 1 hour at room temperature and subsequently the column was washed with buffer. The lysozyme was collected in fractions and the endotoxin content was determined prior to and after the column by means of a chromogenic LAL test (Charles-River Endosafe, Charleston, USA). In addition, the protein retrieval was determined by absorption measurements at 280 nm. The endotoxins were removed up to 85-90% from the solution, as shown in FIG. 3A, and 85-90% of the lysozyme were able to be eluted again from the column by means of washing with usable buffer (FIG. 3B). The column was subsequently washed with 6 ml 5 mM EDTA, 20 mM hepes, 150 mM NaCl, pH 7.5 and 6 ml 1 M NaCl. In order to exclude impurities of the protein fractions after running over the column due to separating p12, the fractions were tested by means of the Western Blot technique for p12. No p12 was able be detected in the fractions.

Example 7

Directed Coupling of p12 to NHS-Activated Carrier Material Column via diaminoethane and N-succinimidyl-iodoacetate (SIA) as Spacer In order to achieve a directed binding to the chromatography carrier material, a bifunctional linker was bonded to NHS-activated surface, which linker made a coupling of p12S3C possible via its free cysteine and iodoacetyl radicals of the bifunctional linker.

NHS-activated sepharose columns (HiTrap NHS-activated HP, 1 ml Amersham-Pharmacia-Biotech) were washed firstly with 6 ml ice cold 1 mM hydrochloric acid, thereafter 1 ml ethylene diamine (10 mg/ml in 0.2 M NaHCO$_3$, 0.5 M NaCl, pH 8.3) was injected and the column was incubated for 30 min at room temperature. After blocking surplus NHS groups with ethanolamine (0.5 M ethanolamine, 0.5 M NaCl, pH 8.3) and washing (0.1 M acetate, 0.5 M NaCl, pH 4.0) of the column, the column was equilibrated with 6 ml borate buffer (50 mM sodium borate, 150 mM NaCl, 5 mM EDTA, pH 8.3). Subsequently, 10 ml N-succinimidyl-iodoacetate (SIA; Pierce, 200 μl SIA parent solution in 10 ml borate buffer; SIA parent solution: 1.4 mg SIA in 1 ml DMSO) was rinsed in a circle over the column for 30 min. The column was thereafter washed with 6 ml borate buffer and p12S3C. (1 mg/ml, 50 ml in borate buffer) was rinsed over the column for 1 hour. Excess iodoacetyl radicals were neutralised with 1 ml cysteine solution (5 mM cysteine in borate buffer, incubation at room temperature for 15 min), before the column with the usable buffers (20 mM hepes, 150 mM NaCl, pH 7.5 or 50 mM tris, 150 mM NaCl, ph 8.5) were equilibrated. The coupling reactions with SIA were implemented in the dark.

The endotoxin removal over this column was tested with lysozyme solutions (3-4 mg/ml in 20 mM hepes, 150 mM NaCl, pH 7.5 or 20 mM tris, 150 mM NaCl, ph 8.5). The lysozyme solutions were spiked with endotoxin from *E. coli* HMS 174 (~500 EU/ml). 0.5 ml protein solution was introduced onto the column, was incubated for 1 hour at room temperature and subsequently the column was washed with buffer. The lysozyme was collected in fractions and the endotoxin content was determined prior to and after the column by means of a chromogenic LAL test (Charles-River Endosafe, Charleston, USA). In addition, the protein retrieval was determined by absorption measurements at 280 nm. The endotoxins were removed up to 90% from the solution, as shown in FIG. 3A, and 75-85% of the lysozyme were able to be eluted again from the column by washing with usable buffer (FIG. 3B). The column was subsequently washed with 6 ml 5 mM EDTA, 20 mM hepes, 150 mM NaCl, pH 7.5 and 6 ml 1 M NaCl. In order to exclude impurities of the protein fractions after running over the column due to separating p12, the fractions were tested for p12 by means of the Western Blot technique. No p12 was able to be detected in the fractions.

Example 8

Removal of Endotoxin from a BSA Solution in the Throughflow Method

HiTrap-NHS activated sepharose (Amersham Biosciences, Uppsala Sweden) was coupled, according to the specification of the producer, non-specifically via primary amino groups with p12. 8 mg p12/ml gel material were thereby immobilised covalently. The thus obtained 1 ml chromatography column was equilibrated with a flow rate of 1 ml/min with 10 ml buffer A (20 mM hepes, pH 7.5, 150 mM NaCl, 0.1 mM CaCl$_2$). Next, 4 ml of a BSA solution (11.5 mg BSA (Carl Roth GmbH, Germany)/ml buffer A) were applied (injection: I) and the throughflow (E) was collected in 2.5 ml fractions. The column was washed subsequently with 15 ml buffer A and the endotoxin bonded to the column was eluted with 7 ml buffer B (20 mM hepes, pH 7.5, 150 mM NaCl, 2 mM EDTA). During washing and elution, respectively 2 ml fractions were collected. After each experiment, the column was regenerated with 20 ml buffer C (20 mM hepes, pH 7.5, 150 mM NaCl, 2 mM EDTA, 0.1% sodium deoxycholate). The endotoxin concentration was determined by a chromogenic Limulus Amoebocyte Lysate (LAL) (Charles-River Endosafe, Charleston, USA) according to the specification of the producer. Determination of the protein concentration was effected by measurement of the UV absorption. The endotoxin removal efficiency was between 95-99% and the protein loss was approximately 6-10%.

Example 9

Removal of Small Endotoxin Quantities from Buffer by Means of Non-Specifically Coupled p12

20 ml NHS-activated sepharose 4 FastFlow (Amersham Biosciences) were washed firstly with ice cold hydrochloric acid and subsequently incubated with 292 mg p12 (7 mg/ml in 25 mM citrate pH 7.0) for 4 hours at room temperature with agitation. Subsequently, the sepharose was washed with 7×80 ml 5 mM citrate pH 2.0 and respectively 1 ml of the washing fractions was dialysed against 5 mM citrate pH 2.0. These dialysates were used in order to quantify the excess p12 in the washing fractions by means of absorption measurement at 280 nm. A charge density of 8.7 mg p12 per 1 ml sepharose was determined. Non-reacted NHS radicals were neutralised by 12 h incubation of the sepharose with 1M tris pH 8.0. Columns with 2 ml volume were filled with this column material and this was stored until use at 4° C. in 20% ethanol.

In 3 parallel tests, respectively 4 ml endotoxin solution (S) were applied onto a column (see FIG. 9). The endotoxin solution comprised endotoxin from E. coli O55:B5 (Charles-River Endosafe, Charleston, USA) in equilibration buffer (20 mM hepes, 150 mM NaCl, 0.1 mM $CaCl_2$, pH 7.5). The endotoxin concentration of this solution was 4.6 EU/ml.

The column was rinsed firstly with 12 ml regeneration buffer (20 mM hepes, 150 mM NaCl, 2 mM EDTA, pH 7.5) and subsequently with 12 ml equilibration buffer. Subsequently, equilibration buffer was introduced once again to the column and 1 ml was fractionated.

The endotoxin solution was applied onto the columns (I) and fractions of 5 ml and 2 ml were collected. Subsequently, the column was regenerated with 4 ml regeneration buffer (B). In the throughflow fractions, no endotoxin could be detected, i.e. the endotoxin impurities were able to be removed completely in all three experiments.

Example 10

Non-Specific Coupling of Biotinylated p12 to Magnetic Streptavidin Beads p12 (3 mg/ml in PBS, 0.05% Tween20) was incubated with sulfo-NHS-LC-LC-biotin (Pierce), in the ratio 1:10 to 1:20 for 1 hour at RT and subsequently was dialysed against buffer (e.g. PBS or 20 mM hepes, 150 mM NaCl, 5 mM EDTA, pH 7.5). NHS-activated biotin binds thereby to primary amino radicals of p12. Subsequently 50 µl biotinylated p12 (1 mg/ml) were added to 1 ml streptavidin beads (MagPrep streptavidin beads, Merck), were agitated at room temperature for 2 h and subsequently excess p12 was removed by washing four times with 1.5 ml 20 mM tris, 10 mM EDTA, pH 7.5.

The endotoxin removal was tested with buffer (20 mM hepes, 150 mM NaCl, pH 7.5) and protein solutions (0.1 mg/ml BSA, 0.1 mg/ml lysozyme, 0.1 mg/ml carbonic anhydrase in 20 mM hepes, 150 mM NaCl, pH 7.5). The buffer and the BSA and lysozyme solution was spiked with 5 EU/ml (endotoxin from E. coli O55:B5, Charles-River Endosafe, Charleston, USA). The carbonic anhydrase solution contained approximately 1 EU/ml. 25 µl magnetic beads with immobilised p12 were added to 200 µl buffer or protein solution, mixed by pipetting up and down and were incubated for 30 min at room temperature. The beads were removed from the solution by means of a magnet, the residue was pipetted off. The endotoxin content of untreated samples and samples incubated with beads was subsequently determined with the LAL test and the protein retrieval was determined by absorption measurement at 280 nm. The endotoxin could be practically completely removed from the buffer (99.9% endotoxin removal, FIG. 4A) and the endotoxin was depleted also from the protein solution by 70-92% (FIG. 4B). The protein retrieval was between 57% and 99% (BSA: 87%, carbonic anhydrase: 99%, lysozyme: 57%; FIG. 4B).

Example 11

Non-Specific Coupling of Biotinylated p12 to Immobilised Streptavidin p12 (3 mg/ml in PBS, 0.05% Tween20) was incubated with sulfo-NHS-LC-LC-biotin (Pierce), in the ratio 1:10 to 1:20 for one hour at RT and subsequently dialysed against buffer (e.g. PBS or 20 mM hepes, 150 mM NaCl, 5 mM EDTA, pH 7.5). NHS-activated biotin thereby binds to primary amino radicals of p12. The biotinylated p12 is subsequently incubated for 1 h at room temperature with chromatography material laden with streptavidin (Immunopure immobilised streptavidin: 6% cross-linked agarose beads) and excess p12 is removed by washing with PBS.

The endotoxin removal was tested with buffer (20 mM tris, 150 mM NaCl, pH 8.0) and BSA (0.5 mg/ml in 20 mM tris, 150 mM NaCl, pH 8.0). Respectively 1 ml buffer or BSA solution was spiked with 10 EU/ml, 50 µl p12 agarose was added, agitation took place for 1 hour at room temperature. The p12 agarose was centrifuged off subsequently and the endotoxin- and protein concentration in the residue was measured. 99% endotoxin could be removed from the buffer and 86% from the BSA solution (FIG. 5). BSA was retrieved up to 90%.

Example 12

Tests via p12 Endotoxin Binding by Means of Surface Plasmon Resonance Measurements Binding of p12 to endotoxin or to bacteria via the liposaccharides in the outer cell membrane was tested by means of surface plasmon resonance measurements (Biacore J). In order to determine the dissociation constant ($K_d$), endotoxin from E. coli O55:B5 (Sigma) was immobilised on a hydrophobic HPA chip corresponding to the instructions of the producer and p12 was injected in various concentrations (FIG. 6A). Binding is measured in relative "response units" (RU), the equilibrium values are plotted against the associated p12 concentrations (FIG. 6B). By adapting the Langmuir adsorption isotherms ($RU=(RU_{max}*[p12])/([p12]+K_d)$) to these data, the $K_d$ value was determined (Table 1). Endotoxin-free buffers were used for the measurements. $K_d$ values in the range of $10^{-7}$ to $10^{-9}$ M were determined for pH values between 6 and 10 (Table 1). The binding was broken again by injection of 1 mM or 5 mM EDTA and the chip was regenerated.

TABLE 1

Dissociation constants of endotoxin on p12 dependent upon the pH value of the solution

| pH | Kd |
|---|---|
| 6.00 | 3.09E−07 |
| 7.50 | 6.85E−08 |
| 8.00 | 5.86E−08 |
| 8.50 | 7.86E−08 |
| 9.00 | 3.29E−08 |
| 10.00 | 1.55E−07 |

In order to test the binding of bacteria to p12, biotinylated p12 was immobilised on streptavidin chips and various E. coli strains were injected. The bacteria were absorbed in PBS for the measurements. E. coli strains were used which have lipopolysaccharides with different polysaccharide components. The polysaccharide part comprises a "core" region which is cross-linked to the lipid A and to the so-called O antigen. The O antigen varies very greatly between different types of bacteria and also strains of bacteria, whilst the "core" region is highly preserved. Strains, which have the "core" region and O antigen (e.g. *E. coli* ), and strains which have a complete "core" region (*E. coli* D21), were bonded by p12, whilst strains with a greatly shortened "core" region (e.g. *E. coli* D21f2) were no longer detected by p12 (FIG. 6C). The binding was able to be broken again by EDTA (5 mM) and the chip was able to be regenerated.

Example 13

Recombinant p12 Constructs

1. Construction of p12 with N-terminal Strep-tag (N-strep-p12): by means of PCR, the nucleotide sequence for the Strep-tag (U.S. Pat. No. 5,506,121) was introduced to the 5' end of the T4p12 gene. A primer was constructed for this purpose for the 5' end of the p12 gene (5'-GAA GGA ACT AGT CATATG GCT AGC TGG AGC CAC CCG CAG TTC GAA AAA GGC GCC AGT AAT AAT ACA TAT CAA CAC GTT-3' (SEQ ID NO:1), which comprises the nucleotide sequence of the Strep-tag at its 5' end (italicised in the sequence) and has a restriction interface (NdeI, underlined in the sequence) such that the gene in the right-hand reading grid can be inserted into the expression plasmid. For the 3' end of the p12 gene, a primer was constructed which introduces, behind the p12 gene, a BamH I restriction interface (italicised in the sequence) (5'-ACG CGC AAA GCT TGT CGA CGG ATC CTA TCA TTC TTT TAC CTT AAT TAT GTA GTT-3'), (SEQ ID NO:2). The PCR was implemented with 40 cycles (1 min 95° C., 1 min 45° C. and 1 min 72° C.). The PCR batch was cut with the restriction endonucleases NdeI and BamHI and the desired fragment was inserted after size fractionation via an agarose gel and elution from the gel into the NdeI and BamHI site of the expression plasmid pET21a. The sequence of the N-strep-p12 gene was checked for its correctness via DNA sequencing. The further steps for the plasmid pNS-T4p12p57 were implemented as described by Burda, M. R. & Miller, S. (Eur J Biochem. 1999 265 (2), 771-778) for T4p12p57. The plasmid pNS-T4p12p57 was then transformed into the expression strain BL21 (DE3).
2. Insertion of an N-terminal cysteine radical in N-strep-p12 (N-strep-S3C-p12 and N-strep-S14C-p12): the insertion of an N-terminal cysteine radical was implemented as described under 1, two new primers for the 5' end being constructed for this purpose. There was used for the N-strep-S3C-p12, the primer 5'-GAA GGA ACT AGT CATATG GCT TGT TGG AGC CAC CCG CAG TTC GAA AAA GGC GCC AGT AAT AAT ACA TAT CAA CAC GTT-3' (SEQ ID NO:3), there was used for the N-strep-S14C-p12, the primer 5'-GAA GGA ACT AGT CATATG GCT AGC TGG AGC CAC CCG CAG TTC GAA AAA GGC GCC TGT AAT AAT ACA TAT CAA CAC GTT-3' (SEQ ID NO:4).
3. Purification of N-strep-p12 protein: the *E. coli* strain BL21 (DE3) with the plasmid pNS.-T4p12p57 was drawn in 2 l shaker cultures (LB medium with ampicillin 100 μg/ml) up to a OD600 of 0.5-0.7 at 37° C. and the expression of the N-strep-p12-protein was induced by addition of 1 mM IPTG (isopropyl-β-thio-galactopyranoside). After incubation at 37° C. for 4 h, the cells were collected. Collected cells from 10 l culture were taken up in 50 ml sodium phosphate, 20 mM pH 7.2, 2 mM MgSO4, 0.1 M NaCl, broken up by French press treatment (20,000 psi) three times and subsequently centrifuged off for 30 min at 15,000 rpm (SS34). After washing twice in the same buffer, the N-strep-p12 protein was extracted from the pellet, the pellet was extracted three times by agitation for 30 min in 40 mM trisHCl pH 8.0, 10 mM EDTA, the batch was centrifuged for 30 min at 15,000 rpm (SS34) and the dissolved NS-p12 was stored in the residue at 4° C. The extraction was repeated twice and the combined residues were applied (IBA GmbH Göttingen) onto a StrepTactin affinity column (15 ml), equilibrated with buffer "W" (100 mM trisHCl pH 8, 1 mM EDTA, 150 mM NaCl). After washing with 5 column volumes of buffer "W", elution took place with three volumes of buffer "W" with 2.5 mM dethiobiotin in buffer "W". After multiple dialysis against buffer "W" and concentration, the concentration and purity of N-strep-T4p12 was determined via SDS-PAGE and UV spectroscopy (Burda et al. 1999). From 10 litres culture, approximately 100 mg N-strep-T4p12 were thus purified.

| Name | Sequence of the tag | |
|---|---|---|
| Nstrep-p12 | MASWSHPQFEKGAS | SEQ ID NO: 5 |
| Nstrep-p12-53C | MACWSHPQFEKGAS | SEQ ID NO: 6 |
| Nstrep-p12-S14C | MASWSHPQFEKGAC | SEQ ID NO: 7 |

The invention claimed is:

1. A method for detecting endotoxin, comprising the steps:
   a) incubating a sample with an isolated p12-similar bacteriophage tail protein in the presence of divalent ions, wherein said p12-similar bacteriophage tail protein binds to highly conserved regions of endotoxin, and
   b) detecting endotoxin bound to said bacteriophage tail protein.

2. The method according to claim 1, further comprising after step a) and prior to step b) the additional step of:
   a') separating the bacteriophage tail protein-endotoxin complex from the sample.

3. The method according to claim 1, wherein detection comprises spectroscopic methods.

4. A method for removing endotoxin from a sample, comprising the steps:
   a) incubating a sample with or bringing a sample in contact with an isolated p12-similar bacteriophage tail protein which is immobilized on a permanent carrier in the presence of divalent ions wherein said p12-similar bacteriophage tail protein binds to highly conserved regions of endotoxin; and
   b) separating bacteriophage tail protein-endotoxin complex from the sample, wherein the permanent carrier comprises filtration media, glass particles, magnetic particles, agarose particles, sedimentation materials or filling materials for chromatography columns.

5. The method according to claim 4, wherein steps a) and b) are implemented in a chromatography column flowthrough method.

6. The method according to claim 4, wherein the bacteriophage tail protein is immobilized on the permanent carrier via coupling groups.

7. The method according to claim 6, the coupling group being a lectin, receptor or anticalin.

8. The method according to claim 6, wherein the coupling group comprises streptavidin or avidin and the bacteriophage tail protein is coupled with biotin or a Strep-tag.

9. The method according to claim 4, wherein the bacteriophage tail protein is immobilized on the permanent carrier covalently via chemical bonds.

10. The method according to claim 1, wherein the bacteriophage tail protein comprises a Strep-tag or a His-tag.

11. The method according to claim 10, wherein the tag comprises an amino acid sequence of SEQ ID NO. 5, 6, or 7.

12. The method according to claim 1, wherein the divalent ions are $Ca^{2+}$ or $Mg^{2+}$ in the range of 0.1 µM to 10 mM.

13. The method according to claim 1, wherein detecting comprises detecting fluorescence-marked endotoxin being displaced from said bacteriophage tail protein in step a).

14. The method according to claim 4, wherein the bacteriophage tail protein comprises a Strep-tag or a His-tag.

15. The method according to claim 14, wherein the tag comprises an amino acid sequence of SEQ ID NO. 5, 6, or 7.

16. The method of claim 1, wherein said p12-similar bacteriophage tail protein binds to the core region or lipid A.

17. The method of claim 4, wherein said p12-similar bacteriophage tail protein binds to the core region or lipid A.

* * * * *